United States Patent [19]

Awwad et al.

[11] Patent Number: 5,856,106

[45] Date of Patent: Jan. 5, 1999

[54] DETERMINATION OF ANTIBODY PRODUCTION AGAINST ADMINISTERED THERAPEUTIC GLYCOPROTEINS, ESPECIALLY MONOCLONAL ANTIBODIES

[75] Inventors: Michel G. Awwad, Hudson, N.H.; Sonny Abraham, Weston, Mass.; Mary E. White-Scharf, Winchester, Mass.; James A. Hope, Hingham, Mass.

[73] Assignee: BioTransplant, Inc., Charlestown, Mass.

[21] Appl. No.: 548,340

[22] Filed: Nov. 1, 1995

[51] Int. Cl.$^6$ ..................................................... G01N 33/53
[52] U.S. Cl. ............................ 435/7.1; 435/7.9; 435/7.92; 435/7.93; 435/7.94; 435/7.95; 435/962; 436/517; 436/518; 436/548; 530/387.5
[58] Field of Search .................................. 435/7.1, 6, 7.5, 435/7.9, 7.92–7.95, 962, 975; 436/506–507, 517, 518, 825, 548; 530/387.5, 389.1, 389.5, 389.9, 806, 868, 388.25

[56] References Cited

U.S. PATENT DOCUMENTS

| | | | |
|---|---|---|---|
| 4,671,958 | 6/1987 | Rodwell et al. | 530/391.9 X |
| 4,741,900 | 5/1988 | Akvarez et al. | 424/85 |
| 4,798,806 | 1/1989 | Kung et al. | 436/548 |
| 4,867,973 | 9/1989 | Goers et al. | 424/85.91 |
| 4,965,069 | 10/1990 | Quash et al. | 424/89 |
| 4,966,999 | 10/1990 | Coughlin et al. | 530/391.5 X |
| 5,057,313 | 10/1991 | Shih et al. | 424/85.91 |

OTHER PUBLICATIONS

Awwad et al. "Modification of monoclonal antibody carbohydrates by oxidation conjugation or deprymannoyrimycin does not interfere with antibody effector functions" Cancer Immunol. Immunotherap (1994) 38:23–30.

Buisy et al., "Minor human antibody response to a mouse and chimeric monoclononal antibody after a single I.V. Infusion in ovarian carcinoma patients . . . " Cancer Immunol. Immunotherap (1995) 40:24–30.

Lin et al., "A flow cytometric method for the detection of the development of antibody to Orthoclone OKT3" J. of Immunol. Methods (1989) 121:197–201.

*Primary Examiner*—Carol A. Spiegel
*Attorney, Agent, or Firm*—Elliot M. Olstein

[57] ABSTRACT

Disclosed are a composition and method for determining the levels of specific immune responsiveness to a glycoprotein in an individual being treated therewith by (i) contacting a body fluid sample obtained from the individual prior to glycoprotein treatment with glycoprotein that has been modified to have an oxidized carbohydrate portion; (ii) contacting a body fluid sample obtained from the individual subsequent to glycoprotein treatment with the glycoprotein that has been modified to have an oxidized carbohydrate portion; and (iii) observing the degree of difference in the specific immune response to the oxidized glycoprotein in the pre- and post-treatment samples.

5 Claims, 6 Drawing Sheets

DETERMINATION OF ANTIBODY PRODUCTION AGAINST ADMINISTERED THERAPEUTIC GLYCOPROTEINS, ESPECIALLY MONOCLONAL ANTIBODIES

BACKGROUND OF THE INVENTION

Glycoproteins, particularly monoclonal antibodies of rat or mouse origin, are increasingly being used for the treatment and diagnosis of cancer, infections, and immunological diseases. When administered to the patient, an immune response is sometimes generated by patients against these antibodies. The response is defined by the difference between the reactivity of the pre- and that of the post-treatment serum or plasma with the infused antibody.

Regulatory agencies require the monitoring and quantification of human immune response to the administered glycoprotein in treated patients. However, pre-dose reactivity of human serum or plasma, in some cases, is high and may interfere with the monitoring and quantification of the specific immune response to the glycoprotein.

In most situations, and although most of the patients are naive with respect to exposure to these proteins, a pre-treatment serum reactivity with the therapeutic protein is typically detected. This reactivity can be attributed to the presence in human serum or plasma of "natural antibodies" reactive with the antibody and in particular with the carbohydrate portion of the administered glycoprotein. Since the pretreatment serum reactivity with the glycoprotein might either conceal or augment the real immune response, reduction of this reactivity is desired.

Awwad M, Strome PG, Gilman SC, and Axelrod HR, Modification of monoclonal antibody carbohydrates by oxidation, conjugation, or deoxymannojirimycin does not interfere with antibody effector function, *Cancer Immunology Immunotherapy*, 38:23–30 (1994) examined site-specific modification of monoclonal antibody (mAB) by periodate oxidation and subsequent conjugation to either a peptide linker/chelator or a cytotoxic drug. These mAB-associated carbohydrates were also modified metabolically by incubating hybridoma cells in the presence of a glucosidase inhibitor (deoxymannojirimycin) to produce high-mannose antibody. It was concluded that modification of mAB carbohydrates did not compromise their in vivo or in vitro biological functions and that, therefore, combination therapy using immunomodulators to enhance the effector functions of site-specific immunoconjugates could be seriously contemplated.

SUMMARY OF THE INVENTION

In accordance with one aspect of the invention it has been observed that the use of oxidized glycoprotein-associated carbohydrates results in a much lower pretreatment reaction with "natural antibodies" as compared to the unmodified forms, i.e., reduces the background level of reactivity of human serum to these glycoproteins so that it is less likely to interfere with an accurate determination of pre- and post-treatment patient reactivities. Modification can be achieved chemically, enzymatically or by the use of glycosylation inhibitors in tissue cultures producing the glycoprotein, e.g., monoclonal antibody. Alternatively, aglycosylated "glycoproteins" can be produced using molecular biology techniques.

Accordingly, the invention provides a method for determining the levels of immune responsiveness to a glycoprotein in an individual being treated therewith which comprises contacting a body fluid sample obtained from said individual prior to glycoprotein treatment with the glycoprotein that has been modified to have an oxidized carbohydrate portion;

contacting a body fluid sample obtained from said individual after glycoprotein treatment with the glycoprotein that has been modified to have an oxidized carbohydrate portion; and observing the degree of difference in the specific binding response of the oxidized glycoprotein with the pre- and post-treatment samples. Preferably the oxidized carbohydrate portion of the modified glycoprotein is oxidized by the presence of aldehyde groups on the carbohydrate portion. It is particularly preferred that the oxidized carbohydrate portion of the modified glycoprotein has at least about three aldehyde groups.

Preferably the glycoprotein for which levels of responsiveness are being determined is an antibody, particularly a xenogeneic antibody or a monoclonal antibody. Preferably the level of responsiveness is measured by an in vitro assay of serum from said individual.

In another aspect the invention provides a composition for determining the levels of specific immune responsiveness to a glycoprotein in pre- and post- treatment samples in an individual being treated therewith which comprises:

the glycoprotein that has been modified to have an oxidized carbohydrate portion; and means for observing the degree of difference in the specific immune response of the oxidized glycoprotein with the pre- and post- treatment samples. Preferably the composition is an in vitro assay composition and the oxidized carbohydrate portion of the modified glycoprotein is oxidized by the presence of aldehyde groups on the carbohydrate portion. It is particularly preferred that the oxidized carbohydrate portion of the modified glycoprotein has at least about three aldehyde groups. Preferably the glycoprotein for which levels of responsiveness are being determined is an antibody, particularly a xenogeneic antibody or a monoclonal antibody.

Conditions for the chemical as well as the enzymatic modification process vary with the level and type of glycosylation of a glycoprotein.

DESCRIPTION OF THE PREFERRED EMBODIMENTS

Figure 1:
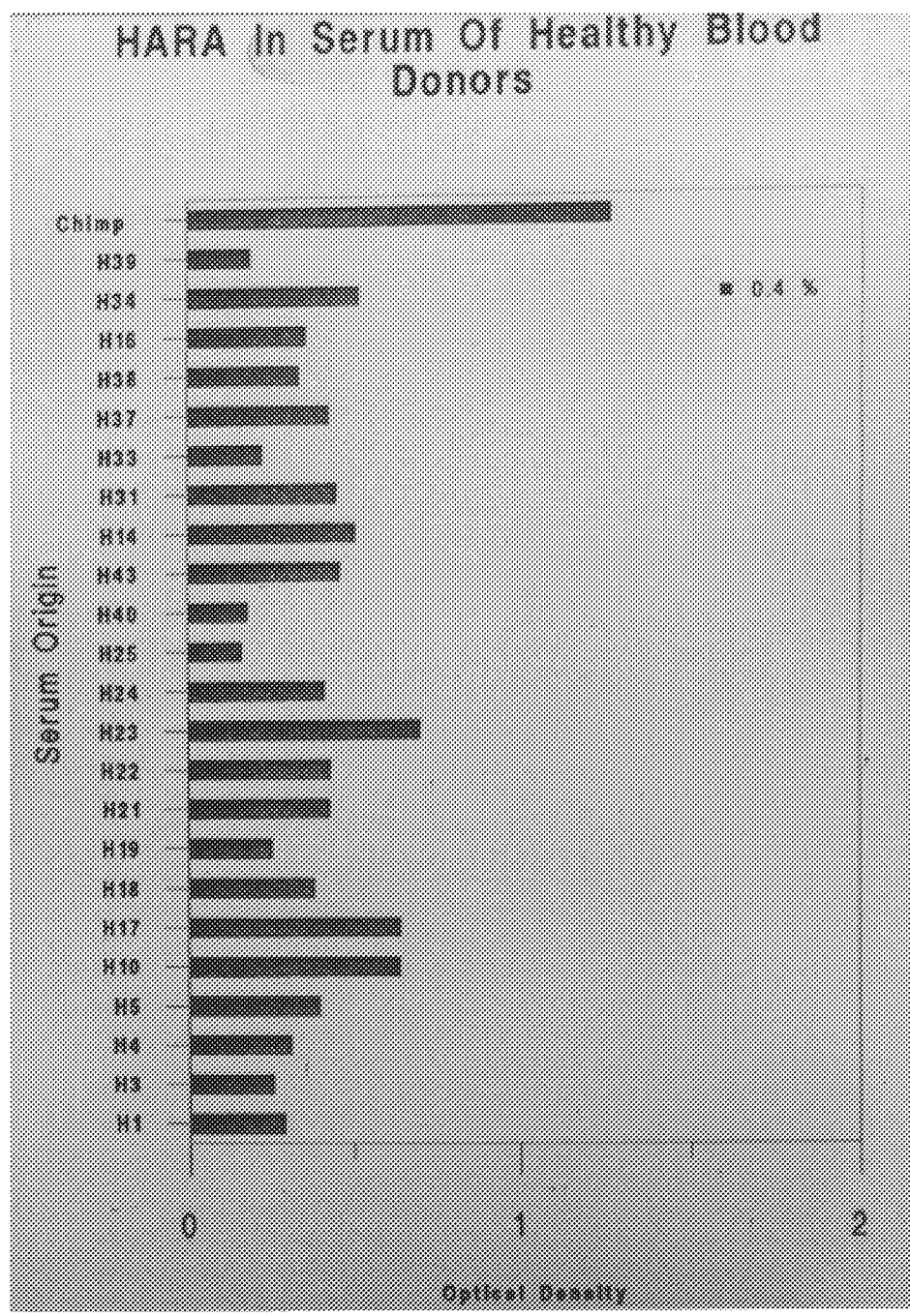
FIG. 1 shows reactivity of different sera from healthy blood donors with rat monoclonal antibody BTI-322. Positive control is hyper-immune serum obtained from chimpanzee immunized with BTI-322 (chimp). Concentration of serum used was 0.4%.

The development of specific binding assay techniques has provided extremely useful analytical methods for determining various substances of diagnostic, medical, environmental and industrial importance which appear in various liquid or solid (e.g., tissue) samples at very low concentrations. Specific binding assays are based on the specific interaction between a bindable analyte under determination and a binding partner therefor, i.e. analyte-specific moiety. The binding of the analyte-specific moiety and interaction of any additional reagents, if necessary, effect a mechanical separation of bound and unbound labeled analyte or affect the label in such a way as to modulate the detectable signal. The former situation is normally referred to as heterogeneous and the latter as homogeneous, in that the latter does not require a separation step.

Where either the analyte or its binding partner is a target antigen or hapten and the other is an antibody or specific binding fragment of such an antibody, the assay is known as an immunoassay.

In conventional label conjugate specific binding assay techniques, a sample of the liquid medium to be assayed is combined with various reagent compositions. Such compositions include a label conjugate comprising a binding component incorporated with a label. The binding component in the conjugate participates with other constituents, if any, of the reagent composition and the ligand in the medium under assay to form a binding reaction system producing two species or forms of the conjugate, e.g., a bound-species (conjugate complex) and a free-species. In the bound-species, the binding component of the conjugate is bound by a corresponding binding partner whereas in the free species, the binding component is not so bound. The amount or proportion of the conjugate that results in the bound species compared to the free species is a function of the presence (or amount) of the analyte to be detected in the test sample.

An alternative format for specific binding assays is the "sandwich" assay protocol in which the target analyte is bound between a first specific binding partner, which is fixed directly or through a linkage group to a solid matrix, and a second specific binding partner, which is associated with a signal generating or labeling system.

Additional immunoassay formats and protocols are also known in the art and are applicable to use in the present invention. Various binding assays using immobilized or immobilizable materials for the direct immobilization of one of the binding participants in a binding assay reaction, e.g., immobilized antigen or antibody, in order to accomplish the desired separation of the bound and free forms of a labeled reagent, have been proposed. In particular, a number of such binding assays have been described wherein an antibody to an antigen to be detected is bound to an immobilizing material such as the inner wall of a test tube or a plastic bead.

For example, in U.S. Pat. No. 4,243,749, a competitive binding assay is disclosed wherein a reaction is carried out in a test tube having a specific antibody to a hapten under determination insolubilized or immobilized on the inner wall of the test tube. The reaction includes a labeled hapten conjugate wherein the quantity of the labeled hapten conjugate which becomes bound to the test tube wall is inversely proportional to the amount of the hapten under determination.

Another of such binding assays is described by U.S. Pat. No. 4,230,683 which discloses a method employing a 6 mm polystyrene bead having antigen or antibody bound thereto wherein the antigen or antibody is reacted with a hapten-conjugated antibody to the antigen or antibody. The bound hapten-conjugated antibody is further reacted with labeled anti-hapten antibody in order to determine the amount of antigen or antibody in a test sample.

Still another of such binding assays is described by U.S. Pat. No. 4,228,237 which discloses a method for the detection and determination of ligands in a liquid medium using enzyme labeled avidin and a biotin labeled reagent in a specific binding process. In this method, the ligand to be detected is contacted with an insoluble phase containing a specific binding substance for the ligand.

In addition to the direct immobilization techniques heretofore described, indirect immobilization by marking or labeling a binding assay reaction participant to be immobilized with a first binding substance, and then adding an immobilized second binding substance, has been proposed.

For example, U.S. Pat. No. 4,298,685 discloses an enzyme immunoassay wherein a sample containing a biological substance under determination is mixed with antibodies to the biological substance tagged with biotin and with an enzyme-labeled form of the substance under assay. An immobilized form of avidin is then added wherein the avidin binds to the biotin-tagged antibody to immobilize the antibody-bound fraction of the enzyme-labeled reagent. Similarly, United Kingdom Patent Application No. GB 2,084,317A discloses an antigen-linked competitive enzyme immunoassay using avidin bound to a solid material and a biotin-labeled antigen. Radiolabeled and enzyme-tagged immunoassays require some type of separation step. Recently, a different approach was disclosed which does not require a separation step and therefore has been referred to as a homogeneous system, in contrast to a heterogeneous system in which separation is essential. U.S. Pat. No. 3,817,837 discloses a competitive binding assay method involving the steps of combining the liquid to be assayed with a soluble complex consisting of an enzyme as a labeling substance covalently bound to the ligand to be detected and with a soluble receptor, usually an antibody, for the ligand; and analyzing for the effect of the liquid to be assayed on the enzymatic activity of the enzyme in the complex.

Still further, the labeled reagent can include other conventional detectable chemical group. Such detectable chemical group can be any material having a detectable physical or chemical property. Such materials have been well-developed in the field of immunoassays and in general any label useful in such methods can be applied to the present invention. Particularly useful are enzymatically active groups, such as enzymes (see Clin. Chem. (1976)22:1243), enzyme substrates (see U.S. Pat. No. 4,492,751), prosthetic groups or coenzymes (see U.S. Pat. Nos. 4,230,797 and 4,238,565), and enzyme inhibitors (see U.S. Pat. No. 4,134, 792); spin labels; fluorescers (see Clin. Chem. (1979) 25:353); chromophores; luminescers such as chemiluminescers and bioluminescers (see U.S. Pat. No. 4,380,580); specifically bindable ligands (e.g., biotin and haptens); electroactive species; and radioisotopes such as $^3H$, $^{35}S$, $^{32}P$, 125I, and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors).

Example 1

Assay Background Reduction Using Monoclonal Antibodies

With Oxidized Carbohydrates

BTI-322, a rat anti-human CD2 antibody, currently is being used in clinical studies.

An assay was developed to measure human anti-rat antibody response (HARA) in patients treated with BTI-322, a rat IgG$_{2b}$ anti-CD2 antibody. However, serum harvested from patients before infusion with the antibody and from blood donors that have not been exposed previously to rat IgG showed reactivity with BTI-322. This pre-dose reactivity may interfere in the monitoring and quantification of HARA. This study was conducted to determine whether modification of antibody-carbohydrates by oxidation can facilitate monitoring and quantification of HARA by reducing the pre-dose antibody binding activity.

The term "hyper-immune animals" relates to chimpanzees that were injected and then boosted, 9 months later, with BTI-322.

The term "pre-immune serum" refers to serum harvested from animals (Chimpanzees) before infusion of BTI-322.

The term "pre-dose serum" refers to serum from patients before infusion of BTI-322 or from healthy blood donors.

Materials

Antibodies: The following antibodies were used in conjunction with the ELISA assay: BTI-322 rat monoclonal anti-human CD2 (BioTransplant, Inc.); unmodified and HRP-conjugated rabbit immunoglobulin to rat immunoglobulin (Dako); HRP-conjugated donkey anti-human IgG antibody (Accurate); mouse anti-rat IgG$_{2b}$ antibody (Imex, MARG2b-3); and a cocktail of HRP-conjugated mouse anti-rat κ chain antibodies (Imex, MARK-1/3-PO).

Biochemicals: Oxidation was achieved by sodium m-periodate (Sigma). The efficiency of oxidation was determined by para-nitrophenyl hydrazine (PNPH, ICN) reaction. O-phenylenediamine Dihydrochloride (OPD, Sigma) at a concentration of 0.091 mg/mL in phosphate citrate buffer with urea hydrogen peroxide (Sigma) was used as an ELISA color development reagent. TWEEN® 20 brand of polyoxyethylene sorbate surfactant (manufactured by ICI) (Sigma) in PBS (Sigma) was used as an ELISA washing buffer and 1% BSA (Sigma) in PBS-TWEEN® brand of polyoxyethylene sorbate surfactant (manufactured by ICI) was used to block ELISA plates. Tris buffer (Sigma) was used for storage of oxidized antibody.

Methods

HARA Assay: Briefly, 96-well plates (certified Maxisorb Nunc-Immuno plates) were coated with 50 μL of 5 μg/mL of unmodified or oxidized BET-322. A decreasing concentration of pre- and hyper-immune chimp sera as well as human serum was loaded onto the coated plates. Bound chimp and human gamma-globulins were detected by donkey anti-human IgG. Color development was then achieved by OPD.

Oxidation: BTI-322 (Lot No. S082/S3), at a concentration of ≧5 mg/mL, was incubated at 770-fold molar ratio with sodium m-periodate. The oxidized antibody was then desalted on a prepacked PD-10 gel filtration column (Pharmacia Biotech). The efficiency of oxidation was determined by measuring the number of aldehyde groups generated. This was achieved by reacting para-nitrophenylhydrazine (PNPH) with the aldehyde groups on the oxidized antibody and then determining the molar ratio of pNPH to BTI-322 by spectrophotometry at 390 nm and 280 nm, respectively, as described in Shrines RL, Fuson RC, and Curtin DY, The systemic identification of organic compounds, a laboratory manual, 5th ed. Wiley, New York, P 126(1967). Molarity was calculated using 208000 and 8100 as the values for the molar extinction coefficients of BTI-322 and pNPH, respectively. A molecule of unmodified (native) and oxidized BTI-322 typically contained less than 1 and ≧3 aldehydes groups, respectively. Using an ELISA, it was shown that the reactivity of pre-treatment serum with oxidized BTI-322 was substantially reduced as compared with that of native BTI-322.

Characteristics and Stability of Oxidized BTI-322:

The biochemical stability of oxidized antibody was compared to that of the unmodified BTI-322 by comparing the HPLC (size exclusion) elution profiles and SDS-PAGE migration patterns of these antibody forms were compared. Briefly, 50 μL of oxidized and unoxidized BTI-322 were loaded onto Water HPLC (Millipore) and eluted with PBS. The A$_{280}$ HPLC elution profiles of the different forms of BTI-322 were compared.

The migration patterns on SDS-PAGE were produced by loading about 5 μg of oxidized or unoxidized BTI-322 under reducing and non-reducing conditions onto 4–20% gels (BioRad). Gels were stained with Coommasie Blue and the migration patterns were then compared.

To assess the functional stability of the oxidized antibody, the reactivity of soluble CD2 as well as the anti-BTI-322 reactivity of Chimpanzee hyper-immune serum, rabbit polyclonal and mouse monoclonal antibodies with the oxidized form was compared to that of the unoxidized form.

The immunoreactivity of BTI-322, i.e., its reactivity with CD2, was assessed using plates coated with recombinant soluble human CD2 (50 μL/well of 5 μg/mL). These plates were loaded with a graded dose of oxidized and unoxidized BTI-322. Captured antibodies were then detected by rabbit immunoglobulin to rat immunoglobulin conjugated to HRP (DAKO). Color development was achieved using the substrate o-phenylenediamine dihydrochloride (OPD). Reactivity of the two forms of BTI-322 to rabbit polyclonal antibody was determined in an assay similar to that of immunoreactivity except that the capture antibody was unconjugated rabbit immunoglobulins to rat immunoglobulins.

Reactivity with mouse monoclonal antibodies was determined by using mouse anti-rat IgG2b (MARG2b-3, IMEX) to capture the two forms of BTI-322 and HRP-conjugated mouse monoclonal antibodies to rat κ chain to detect captured antibodies. Color development was achieved, as usual, using OPD.

Human and Chimpanzee Serum: Chimpanzee serum was collected from 2 animals 14 days after being boosted with BTI-322, approximately 9 months after the priming dose. Day 14 sera were pooled and used as positive control in every experiment on every plate. Chimpanzee serum was diluted at first 50-fold, starting concentration, followed by 7 five-fold dilutions. Dilution was achieved in PBS-TWEEN brand surfactant (0.5%).

Human serum was collected from healthy blood donors that were naive to rat immunoglobulin. In other words, these donors had no documented previous exposure to rat immunologlobulin. The reactivity of human serum with BTI-322 was assessed using HARA assay (see above).

Data analysis: ELISA data were analyzed by comparing averages of triplicates of optical density readings. HPLC data were analyzed by comparing the A$_{280}$ elution profile of unmodified BTI-322 to that of the oxidized form. This involved comparing the proportions of monomer in the different preparations. SDS-PAGE data were analyzed by comparing the number of bands and the migration pattern of the different BTI-322 forms under reduced and non-reduced conditions.

Results

Reactivity of Human and Chimpanzee Serum with BTI-322:

Reactivity of Pre- and Hyper-Immune Chimpanzee Serum with BTI-322. Antibodies generated against BTI-322 following infusion into patients must be monitored and quantified. Since patients' sera were not available, pooled hyper-immune sera from 2 chimps that were injected with BTI-322 and then boosted about 9 months later were used as positive control. Table 1 shows the reactivity in a HARA assay of pre- and hyper-immune chimpanzee sera with BTI-322. Optical density readings obtained using hyper-serum were significantly higher than those obtained using pre-immune chimp serum. This indicates that hyper-immune serum contains anti-BTI-322 antibodies. Note that serum harvested from chimpanzees before injecting BTI-322 (pre-immune) had some reactivity with BTI-322. The addition of BTI-322 to hyperimmune chimpanzee serum reduced detectable HARA to the pre-dose level. This demonstrates the specificity of the interaction of chimpanzee serum with BTI-322.

TABLE 1

Reactivity of Pre- and Hyper-Immune Chimpanzee Serum with BTI-322

| Serum Concentration | Hyper-Immune | Dose of BTI-322 (µg/mL) | | | Pre-Immune Chimp Pre- |
|---|---|---|---|---|---|
| (%) | Chimp | 80.5 | 8.7 | 0.87 | dose |
| 0.4 | 0.715 | 0.379 | 0.544 | 0.639 | 0.203 |
| 0.08 | 0.642 | 0.305 | 0.35 | 0.547 | 0.297 |
| 0.016 | 0.495 | 0.135 | 0.203 | 0.251 | 0.285 |
| 0.0032 | 0.241 | 0.03 | 0.08 | 0.099 | 0.175 |
| 0.00064 | 0.097 | 0.019 | 0.021 | 0.036 | 0.06 |
| 0.000128 | 0.037 | 0 | 0.025 | 0.013 | 0.024 |

Reactivity of healthy donor sera with BTI-322:

Similar to chimpanzee pre-immune serum, sera harvested from healthy blood donors with no documented previous exposunce to rat immunoglobulin showed varied level of reactivity with BTI-322 (FIG. 1).

Oxidation of BTI-322: At least three different batches of oxidized antibody were produced by incubation of BTI-322, in complete darkness, with sodium m-periodate for 1 hour. Oxidized antibody was then desalted on prepacked G-23m SEPHADEX® brand of polyglucose polymer crosslinked with epichlorohydrin in columns (manufactured by Pharmacia, Inc.). After two rounds of oxidation, the molar ration of PNPH to oxidized BTI-322 was 3, 4 and 10 as compared to 0.6 of un-oxidized control BTI-322. These results indicate that whereas no free aldehyde groups could be found in un-oxidized BTI-322, 3-10 groups could be found in oxidized antibody. These results indicate that oxidation was successful.

Biochemical Stability of Oxidized BTI-322

FIGS. 2A–2D shows the size exclusion profiles ($A_{280}$) of batches of oxidized BTI-322 (FIGS. 2A and 2B) and that the Reference Standard. HPLC profile of Reference Standard (FIG. 2C) shows that ≧95% of the same consisted of monomer. In addition to the monomer peak, oxidized BTI-322 ion profiles showed a second peak which constituted about or 27%, respectively of the two preparations. Probably, this peak consists mainly of BTI-322 aggregate. Based on the retention time, this aggregate consists mainly of BTI-322 dimers.

Figure 2A:
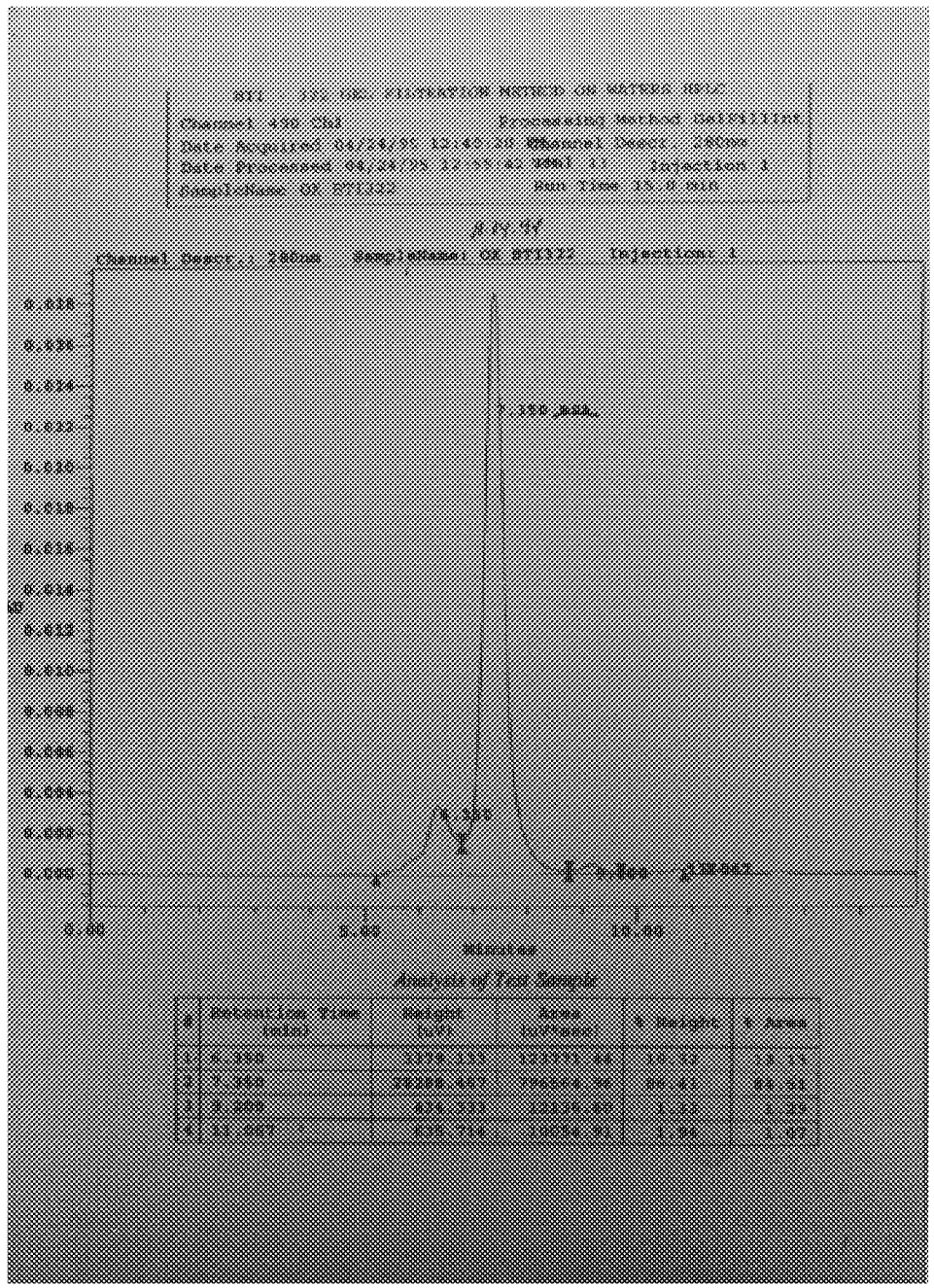
FIGS. 2A–2D show the $A_{280}$ HPLC profiles of two batches of oxidized BTI-322 (FIGS. 2A and 2B), and that of the unoxidized BTI-322 Reference Standard (FIG. 2C) and molecular weight markers (FIG. 2D). The HPLC profile of Reference Standard BTI-322 shows that $\geq 95\%$ of the preparation consisted of monomer. In addition to the monomer peak (84% or 70%), oxidized BTI-322 elution profiles showed a second peak which constituted about 13% or 27% of the sample, respectively. Probably, this peak consists of aggregated BTI-322. Based on the retention time, this fraction consists mainly of BTI-322 dimers.

FIG. 2A shows the $A_{280}$ Waters HPLC profile of a first batch of oxidized BTI-322, where the reported test sample analysis was as follows:

| # | Retention Time (min) | Height (uV) | Area (uV*sec) | % Height | % Area |
|---|---|---|---|---|---|
| 1 | 6.350 | 3379.133 | 123771.44 | 10.32 | 13.13 |
| 2 | 7.350 | 28286.467 | 796564.96 | 86.41 | 84.51 |
| 3 | 9.200 | 434.333 | 12136.60 | 1.33 | 1.29 |
| 4 | 11.067 | 635.714 | 10054.91 | 1.94 | 1.07 |

Figure 2B:
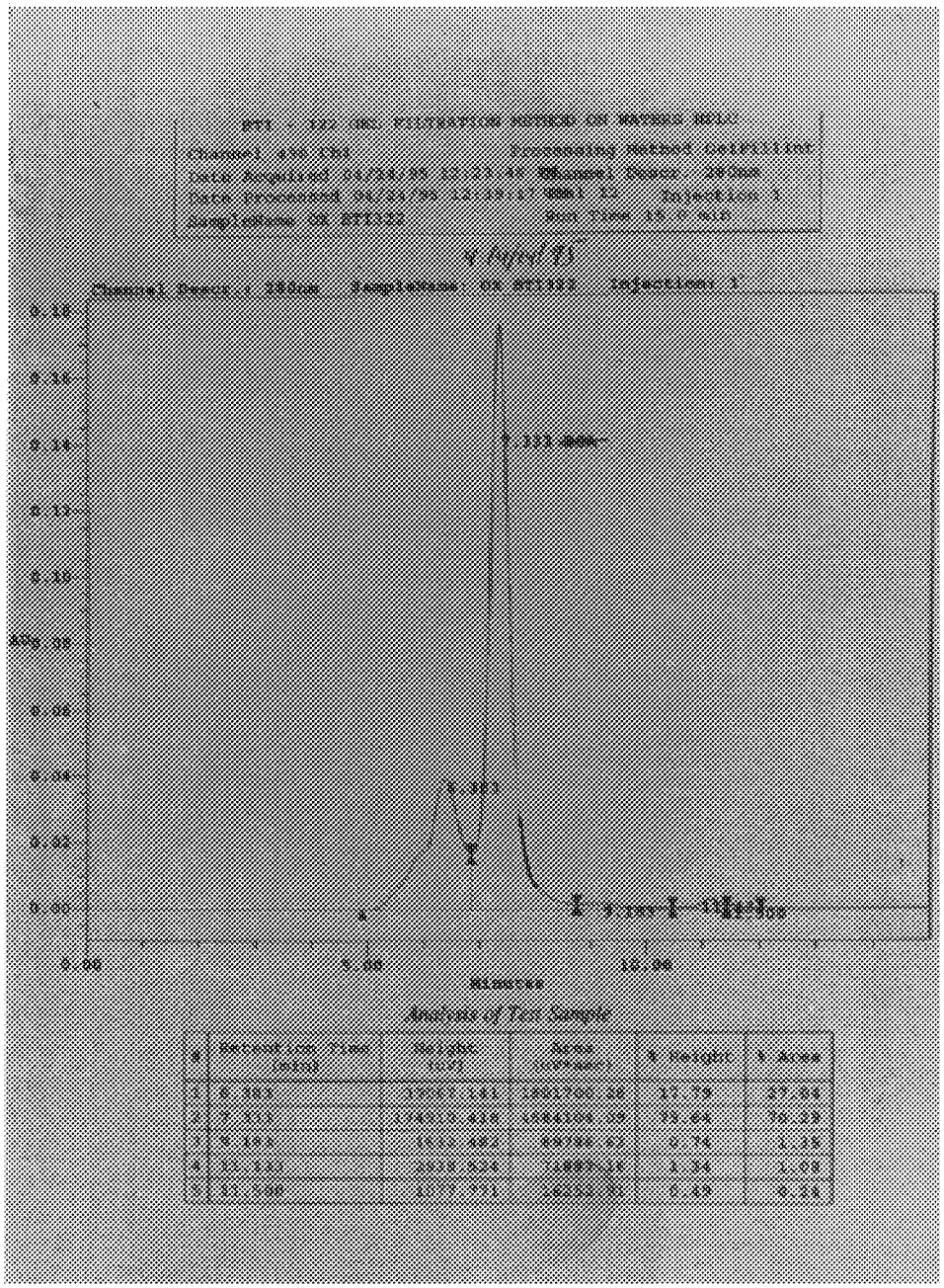

FIG. 2B shows the $A_{280}$ Waters HPLC profile of a second batch of oxidized BTI-322, where the reported test sample analysis was as follows:

Analysis of Test Sample

| # | Retention Time (min) | Height (uV) | Area (uV*sec) | % Height | % Area |
|---|---|---|---|---|---|
| 1 | 6.383 | 39067.141 | 1801700.26 | 17.79 | 27.04 |
| 2 | 7.333 | 174910.418 | 4684104.09 | 79.64 | 70.29 |
| 3 | 9.183 | 1632.482 | 89786.63 | 0.74 | 1.35 |
| 4 | 11.133 | 2938.524 | 71887.16 | 1.34 | 1.08 |
| 5 | 11.500 | 1077.771 | 16252.91 | 0.49 | 0.24 |

Figure 2C:
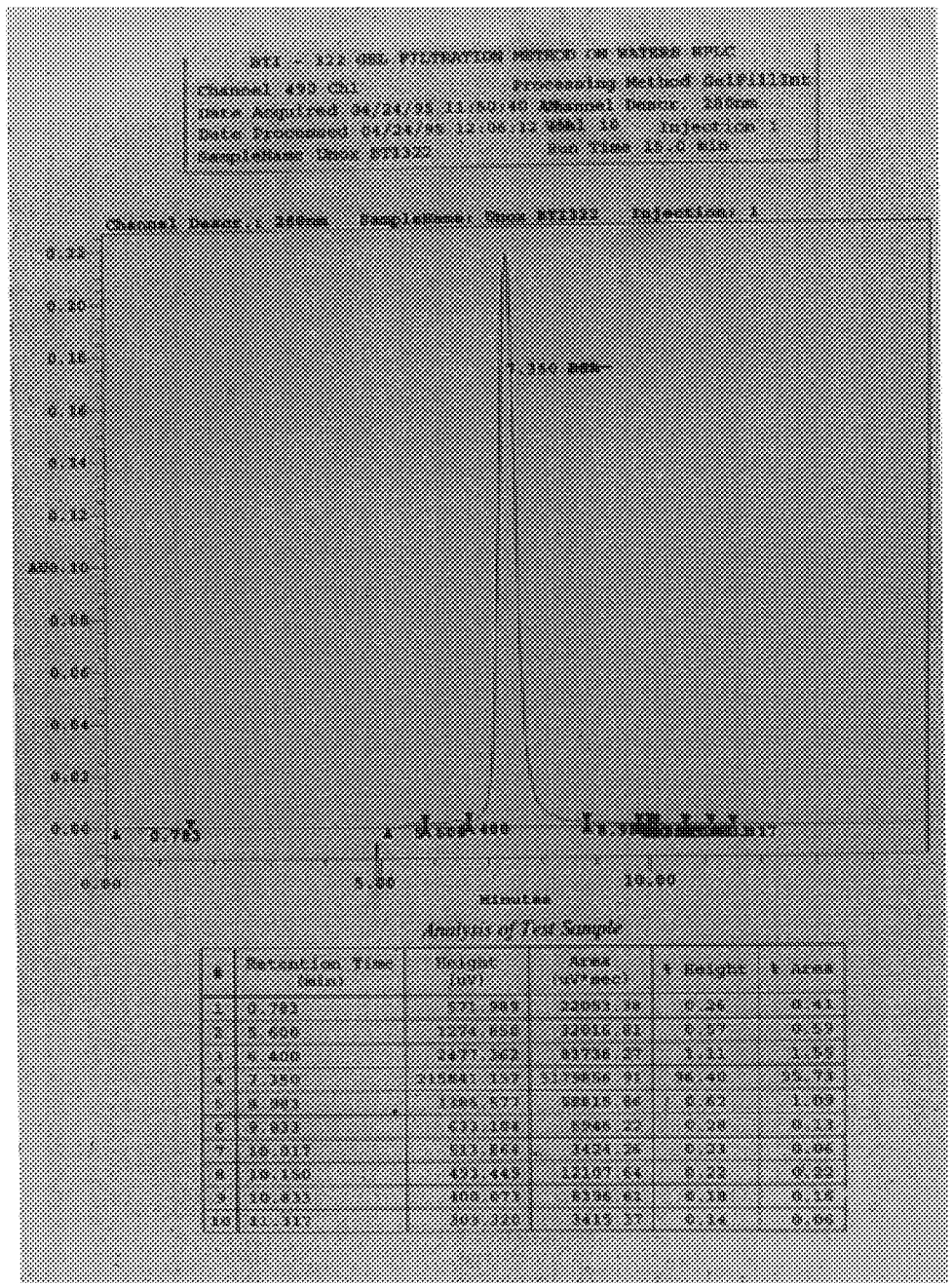
Figure 2D:
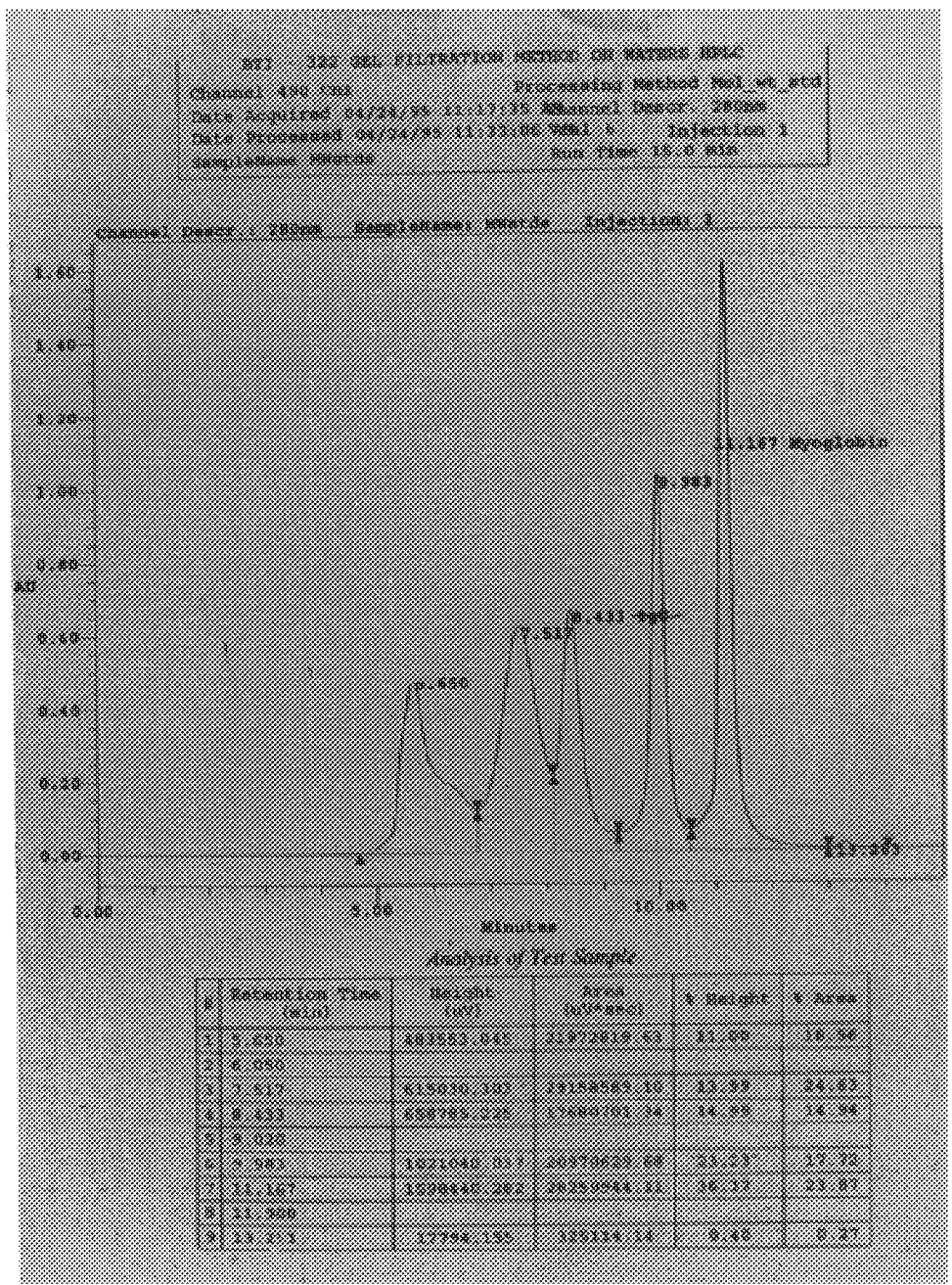

FIG. 2C shows the $A_{280}$ Waters HPLC profile of an unoxidized BTI-322, where the reported test sample analysis was as follows:

Analysis of Test Sample

| # | Retention Time (min) | Height (uV) | Area (uV*sec) | % Height | % Area |
|---|---|---|---|---|---|
| 1 | 0.783 | 571.989 | 22053.38 | 0.26 | 0.41 |
| 2 | 5.600 | 1274.850 | 32016.81 | 0.57 | 0.59 |
| 3 | 6.400 | 2477.362 | 83736.27 | 1.11 | 1.55 |
| 4 | 7.350 | 215841.157 | 5179856.91 | 96.40 | 95.73 |
| 5 | 8.983 | 1385.577 | 58815.86 | 0.62 | 1.09 |
| 6 | 9.833 | 633.184 | 6946.22 | 0.28 | 0.13 |
| 7 | 10.017 | 513.864 | 3424.26 | 0.23 | 0.06 |
| 8 | 10.150 | 493.449 | 12107.64 | 0.22 | 0.22 |
| 9 | 10.833 | 400.073 | 8396.61 | 0.18 | 0.16 |
| 10 | 11.317 | 303.320 | 3415.37 | 0.14 | 0.06 |

FIG. 4D shows the $A_{280}$ Waters HPLC profile of molecular weight standards, where the reported test sample analysis was as follows:

Analysis of Test Sample

| # | Retention Time (min) | Height (uV) | Area (UV*sec) | % Height | % Area |
|---|---|---|---|---|---|
| 1 | 5.650 | 483553.045 | 21972819.63 | 11.00 | 18.56 |
| 2 | 6.050 | | | | |
| 3 | 7.517 | 615030.303 | 29158589.10 | 13.99 | 24.63 |
| 4 | 8.433 | 658785.225 | 17680701.34 | 14.99 | 14.94 |
| 5 | 9.020 | | | | |
| 6 | 9.983 | 1021040.037 | 20970629.68 | 23.23 | 17.72 |
| 7 | 11.167 | 1598440.282 | 28259944.11 | 36.37 | 23.87 |
| 8 | 11.900 | | | | |
| 9 | 13.293 | 17794.155 | 325114.14 | 0.40 | 0.27 |

Figure 3A:
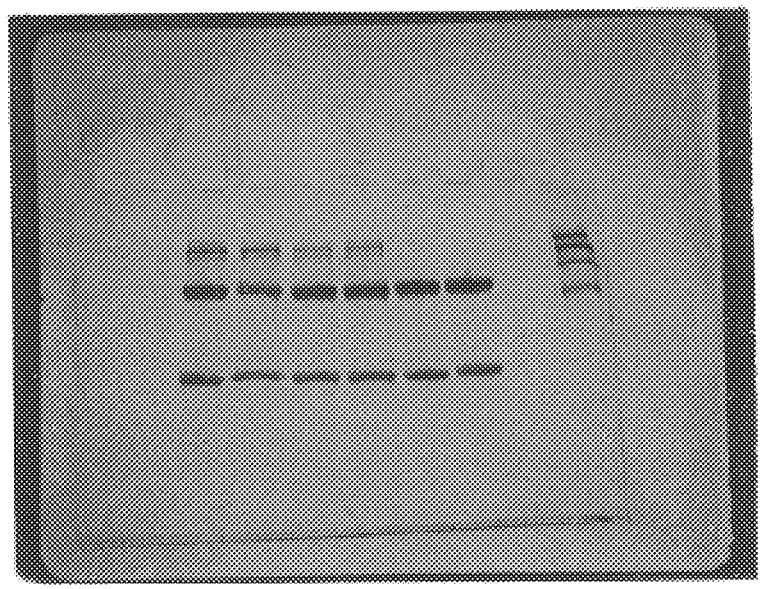
FIGS. 3A and 3B show that aggregates detected by HPLC were also detected by SDS-PAGE under non-reducing (FIG. 3B) as well as reducing (FIG. 3A) conditions. Oxidized BTI-322, with the exception of an additional aggregate band, has a similar migration pattern and the same number of bands as the Reference Standard.
Figure 3B:
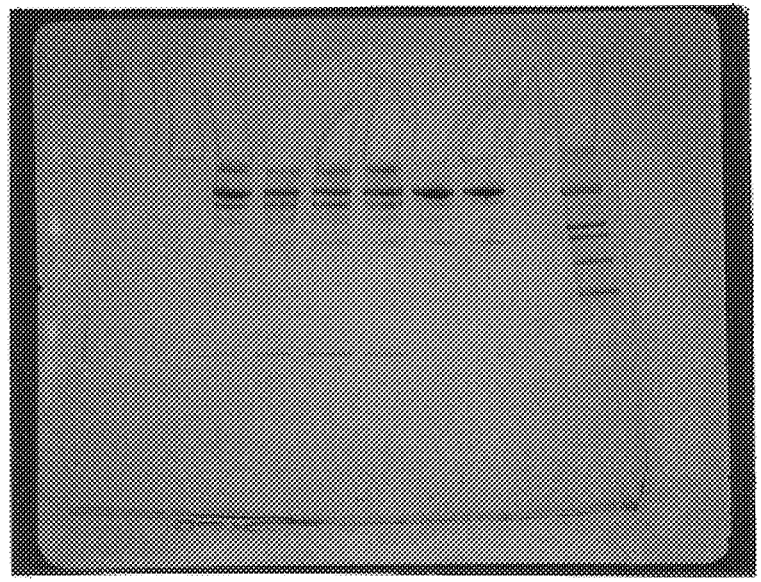

FIGS. 3A and 3B show the SDS-PAGE migration pattern of oxidized [Lanes 8, 7, 6 and 5], unoxidized [Lanes 3 and 4 (Reference Standard)], sample buffer (Lane 2), and molecular weight standards (Lane 1) under reducing (FIG. 3A) and no-reducing (FIG. 3B) conditions. Under non-reduced as well as reduced conditions, oxidized BTI-322 has an identical migration pattern and the same number of bands as the Reference Standard.

The above results indicate that oxidation did not alter significantly the biochemical characteristics of BTI-322.

Functional Stability of Oxidized BTI-322:

To test whether oxidation has affected the capacity of BTI-322 to bind CD2, a graded concentration of Reference Standard and the different batches of oxidized BTI-322 were loaded onto plates coated with recombinant soluble human CD2. Captured antibody was then detected using HRP-conjugated rabbit anti-rat immunoglobulin. Since equivalent optical density readings (Tables 2 and 3) were observed for oxidized and un-oxidized antibody, oxidation, therefore, did not affect binding of BTI-322 to CD2.

TABLE 2

Reactivity of Oxidized BTI-322 (Batch 1) with CD2

| BTI-322 Concentration | Optical Density of BTI-322 | |
|---|---|---|
| (ng/ml) | Oxidized | Reference |
| 10,000 | 0.483 | 0.397 |
| 5,000 | 0.5236 | 0.441 |
| 2,500 | 0.499 | 0.414 |
| 1,250 | 0.471 | 0.387 |
| 625 | 0.452 | 0.356 |
| 312.5 | 0.376 | 0.312 |
| 156.25 | 0.324 | 0.284 |
| 78.125 | 0.197 | 0.258 |
| 39.063 | 0.194 | 0.205 |
| 19.531 | 0.213 | 0.199 |
| 9.766 | 0.204 | 0.187 |
| 4.883 | 0.194 | 0.197 |
| Blank | 0.186 | 0.186 |

TABLE 3

| BTI-322 Concentration | Optical Density of BTI-322 | |
|---|---|---|
| (ng/ml) | Oxidized | Reference |
| 10,000 | 0.476 | 0.421 |
| 5,000 | 0.442 | 0.377 |
| 2,500 | 0.424 | 0.362 |
| 1,250 | 0.389 | 0.318 |
| 625 | 0.322 | 0.3 |
| 312.5 | 0.269 | 0.13 |
| 156.25 | 0.221 | 0.138 |
| 78.125 | 0.149 | 0.162 |
| 39.063 | 0.053 | 0.078 |
| 19.531 | 0.048 | 0.044 |
| Blank | 0.189 | 0.189 |

To test whether oxidation modified the epitopes recognized by polyclonal rabbit immunoglobulin to rat immunoglobulin, plates coated with the polyclonal antibody were loaded with graded concentrations of both forms of BTI-322. Equivalent optical density readings were obtained using both forms of BTI-322 (Table 4). This indicates that oxidation did not change the epitopes that are recognized by polyclonal rabbit anti-rat antibodies.

TABLE 4

Reactivity of Polyclonal Rabbit
Anti-rat Antibody with Oxidized BTI-322 (Batch 1)

| BTI-322 Concentration | | |
|---|---|---|
| (ng/ml) | Oxidized | Reference |
| 10,000 | 0.656 | 0.664 |
| 5,000 | 0.681 | 0.674 |
| 2,500 | 0.609 | 0.642 |

TABLE 4-continued

Reactivity of Polyclonal Rabbit
Anti-rat Antibody with Oxidized BTI-322 (Batch 1)

| BTI-322 Concentration | | |
|---|---|---|
| (ng/ml) | Oxidized | Reference |
| 1,250 | 0.647 | 0.633 |
| 625 | 0.661 | 0.658 |
| 312.5 | 0.607 | 0.637 |
| 156.25 | 0.594 | 0.649 |
| 78.125 | 0.49 | 0.562 |
| 39.06 | 0.389 | 0.361 |
| 19.53 | 0.305 | 0.234 |
| 0 | 0.057 | 0.057 |

The effect of oxidation of BTI-322 on specific epitopes recognized by mouse monoclonal antibodies to rat $IgG_{2b}$ and rat κ chain was determined. MARG2b-3 (anti-rat α-2b) coated plates were loaded with oxidized and un-oxidized BTI-322 and the captured antibodies were detected by MARK-1/3-PO anti-rat κ). Results in Table 5 show that the optical density readings of the two forms of antibodies were equivalent. This indicates that oxidation did not modify epitopes recognized by mouse monoclonal antibodies.

TABLE 5

Reactivity of Mouse Monoclonal
Antibodies with Oxidized BTI-322

| BTI-322 Concentration | | |
|---|---|---|
| (ng/ml) | Reference | Oxidized |
| 10,000 | 0.496 | 0.512 |
| 5,000 | 0.469 | 0.495 |
| 2,500 | 0.475 | 0.456 |
| 1,250 | 0.460 | 0.442 |
| 625 | 0.416 | 0.463 |
| 312.5 | 0.388 | 0.403 |
| 156.25 | 0.374 | 0.315 |
| 78.125 | 0.292 | 0.256 |
| 39.06 | 0.187 | 0.162 |
| 19.53 | 0.115 | 0.096 |
| 0 | 0.070 | 0.07 |

The effect of oxidation on the specific anti-BTI-322 reactivity in hyperimmune Chimpanzee serum was tested by performing a HARA assay using plates coated with either un-oxidized or oxidized BTI-322. Results in Table 6 show that optical density readings obtained using a serial dilution of hyperimmune Chimpanzee serum in both plates were equivalent. This indicates that oxidation did not have an effect on the specific anti-BTI-322 reactivity.

In addition, results in Table 6 also demonstrate that oxidation of BTI-322 can cause 5–20 fold reduction in the reactivity of BTI-322 with serum from an individual (H23) that is naive to rat gamma-globulin.

TABLE 6

Reactivity of Chimpanzee serum with oxidized BTI-322

| Serum Concentration | Reference Standard | | Oxidized | | Oxidized | |
|---|---|---|---|---|---|---|
| (1%) | H23 | Chimp | H23 | Chimp | H23 | Chimp |
| 2 | 0.307 | ND | 0.179 | ND | 0.196 | ND |
| 0.4 | 0.306 | ND | 0.123 | ND | 0.135 | ND |
| 0.08 | 0.205 | 0.543 | 0.058 | 0.520 | 0.063 | 0.537 |
| 0.016 | 0.097 | 0.376 | 0.019 | 0.326 | 0.020 | 0.347 |

TABLE 6-continued

Reactivity of Chimpanzee serum with oxidized BTI-322

| Serum Concentration (1%) | Reference Standard | | Oxidized | | Oxidized | |
|---|---|---|---|---|---|---|
| | H23 | Chimp | H23 | Chimp | H23 | Chimp |
| 0.0032 | 0.037 | ND | 0.002 | ND | 0.005 | ND |
| 0 | 0.054 | 0.054 | 0.054 | 0.054 | 0.054 | 0.054 |

Conclusions

In summary, neither the biochemical nor the functional stability of BTI-322 were altered by oxidation. HPLC profile and SDS-PAGE migration patterns of un-oxidized and oxidized BTI-322 were equivalent. Binding of BTI-322 to its antigen (recombinant soluble human CD2) was not modified by oxidation. Binding of mono- and polyclonal antibodies to rat determinants of BTI-322 was not modified by oxidation. Binding of specific chimpanzee anti-BTI-322 antibody to BTI-322 was not modified by oxidation. Oxidation can cause a reduction of the pre-dose reactivity of human serum with BTI-322. The reactivity of the oxidized antibody with serum from healthy blood volunteers was then determined. The results demonstrate that modification of antibody-associated carbohydrates by oxidation can cause 5–20-fold reduction in the level of the pre-dose reactivity of human serum with BTI-322.

What is claimed is:

1. An in vitro process for determining production in an individual of antibody against a non-oxidized glycosylated antibody administered to said individual comprising:

determining by an in vitro immunoassay said antibody against said non-oxidized glycosylated antibody in a sample derived from said individual, said immunoassay employing as a binder for said antibody an oxidized form of said glycosylated antibody wherein the carbohydrate portion thereof is oxidized.

2. The process of claim 1 wherein the glycosylated antibody is an anti T lymphocyte antibody.

3. The process of claim 2 wherein the anti T lymphocyte antibody is an anti CD2 antibody.

4. The process of claim 1 wherein said determining is performed after treatment of said individual with said glycosylated antibody.

5. The process of claim 4 wherein the determined antibody is compared to antibody values determined for said individual by another immunoassay on a sample derived from said individual prior o the treatment, said another immunoassay employing as a binder an oxidized form of the said glycosylated antibody wherein the carbohydrate portion thereof is oxidized.

* * * * *

UNITED STATES PATENT AND TRADEMARK OFFICE
CERTIFICATE OF CORRECTION

PATENT NO. : 5,856,106
DATED : January 5, 1999
INVENTOR(S) : Awwad, et. al.

It is certified that error appears in the above-identified patent and that said Letters Patent is hereby corrected as shown below:

In Claim 5, Column 12, Line 22:

Replace "prior o the" with --prior to the--.

Signed and Sealed this

Sixth Day of April, 1999

Attest:

Q. TODD DICKINSON

Attesting Officer

Acting Commissioner of Patents and Trademarks